United States Patent [19]

Kuchner et al.

[11] 4,172,119

[45] Oct. 23, 1979

[54] FUNGICIDE

[75] Inventors: Karl Kuchner, Bad Durkheim; Josef B. Pawliczek, Speyer; Ernst-Heinrich Pommer; Dietrich Schlotterbeck, both of Limburgerhof; Wolfgang Sliwka, Weinheim; August Wigger, Waldsee, all of Fed. Rep. of Germany

[73] Assignee: BASF Aktiengesellschaft, Fed. Rep. of Germany

[21] Appl. No.: 879,721

[22] Filed: Feb. 21, 1978

[30] Foreign Application Priority Data

Mar. 2, 1977 [DE] Fed. Rep. of Germany ....... 2708977

[51] Int. Cl.$^2$ .......................... A61K 9/50; A01N 9/00
[52] U.S. Cl. ......................................... 424/32; 424/33; 424/34; 424/35; 424/36; 424/37
[58] Field of Search .................... 252/316; 424/14, 16, 424/19-22, 32-37

[56] References Cited

U.S. PATENT DOCUMENTS

| 2,800,458 | 7/1957 | Green | 252/316 |
|---|---|---|---|
| 3,429,827 | 2/1969 | Ruus | 252/316 |

FOREIGN PATENT DOCUMENTS

| 1164152 | 2/1964 | Fed. Rep. of Germany . |
|---|---|---|
| 2213755 | 3/1972 | Fed. Rep. of Germany . |
| 2119933 | 11/1972 | Fed. Rep. of Germany . |
| 1427085 | 2/1966 | France . |
| 2194483 | 3/1974 | France . |

OTHER PUBLICATIONS

Chem. Abstr. 61 #13321a (1964) of Ger. 1,164,152 Feb. 27, 1964, Sanne et al, "Fungicidal Morphocines".
Chem. Abstr. 65 #10757d (1966) of Fr. 1,427,085 Feb. 4, 1966, Vandegaer "Plastic Capsules" (Counterpart of Ger. Das 1,519,925 and Brit. 1,091,141).
Chem. Abstr. 78 #31019c (1973) of Ger. 2,119,933 Nov. 9, 1972, Baum et al. "Microcapsules" (Counterpart of Brit. 1,375,118 and Can. 968,641).
Chem. Abstr. 81 #122101B (1974), of Fr. Demande 2,194,483 Mar. 1, 1974 BASF "Microcapsules" (Counterpart of Ger. Dos 2,237,503).
Chem. Abstr. 80 #54545b (1974) of Ger. Off. 2,213,755 Oct. 4, 1973, Sliwka et al. "Microcapsule Copy Paper" (Counterpart of Brit. 1,420,175).

*Primary Examiner*—Shep K. Rose
*Attorney, Agent, or Firm*—Keil & Witherspoon

[57] ABSTRACT

A new valuable fungicide based on N-tridecyl-2,6-dimethylmorpholine as the active ingredient, the said ingredient being in the form of microcapsules of which the wall consists of a polymer while the core contains the active ingredient.

5 Claims, No Drawings

FUNGICIDE

The present invention relates to a fungicide based on N-tridecyl-2,6-dimethylmorpholine, in which the active ingredient is in the form of microcapsules.

The use of N-tridecyl-2,6-dimethylmorpholine (tridemorph) as a fungicide has been disclosed in German Patent No. 1,164,152.

The high vapor pressure of the active ingredient causes losses of the latter when used in climatic regions having fairly high average temperatures, since a part of the active ingredient vaporizes before it can exert its fungicidal action. Hence, a second application of active ingredient is in most cases necessary after some time.

It is an object of the present invention to avoid these disadvantages.

We have found that a fungicide based on N-tridecyl-2,6-dimethylmorpholine as the active ingredient does not suffer from these disadvantages if the active ingredient is in the form of microcapsules which contain the active ingredient in their core whilst their walls consist of a crosslinked or non-cross-linked synthetic or natural polymer or a mixture of such polymers, the wall formation being effected by coacervation or by some other type of deposition of wall material or by a wall-forming reaction at the interface between the capsule core and the surrounding medium.

Each microcapsule is a separate reservoir of active ingredient. The capsule walls reduce the rate of vaporization of the active ingredient. This results in a depot action, because a given amount of active ingredient exhibits a fungicidal action for a longer period after application to the plant, and also results in controlled liberation of the active ingredient over a substantial period of time, since the vaporization of the active ingredient can be delayed to a greater or lesser extent depending on the nature of the microcapsules.

When using the non-encapsulated active ingredient at substantial concentrations, phytotoxic phenomena are sometimes observed with certain plants. These are not observed when using the fungicide according to the invention, which substantially broadens the scope of the active ingredient.

The rate of vaporization of the active ingredient from the microcapsule can be regulated by varying the nature of the wall material, the wall thickness, the active ingredient/wall material ratio and the degree of crosslinking of the microcapsule wall.

The nature of the wall material essentially depends on the encapsulation process. The following may be mentioned as examples:

Encapsulation by the coacervation process, for example as described in U.S. Pat. No. 2,800,457. The wall materials used are crosslinked natural polymers, e.g. gelatin or gum arabic.

Encapsulation by the interfacial condensation process (U.S. Pat. No. 3,577,515, German Published Application DAS No. 1,519,925, German Laid-Open Application DOS No. 1,444,415 and U.S. Pat. No. 3,429,827). The wall materials used in this process are nylons obtained by polycondensing terephthalic acid dichloride with a diamine/triamine mixture.

Encapsulation by the phase separation process as described in German Laid-Open Applications DOS Nos. 2,119,933 and 2,237,503. This process is preferred. It employs a crosslinked acrylate-based copolymer as the wall material.

The microcapsules obtained on encapsulation have diameters ranging from 0.01 to 5,000 $\mu$m. Microcapsules with diameters of from 0.1 to 50 $\mu$m are preferred. The capsules may be in the form of individual capsules or capsule agglomerates.

Instead of just the active ingredient, the capsules may also contain mixtures with other active ingredients or with compounds which are miscible with the active ingredient and inert toward the core material and the wall material. These include, for example, high-boiling solvents (100°–250° C.), such as various types of plasticizer, e.g. diethylhexyl phthalate and diisobutyl phthalate, various polyethylene waxes, montan waxes. They modify the viscosity of the active ingredient in the capsules. Mixtures of these active ingredients with a high-boiling liquid which is inert toward the wall material and toward the active ingredient are preferred. The microcapsule core can consist of any mixture of tridemorph and inert component, but a proportion of from 0 to 50% by weight of the latter, based on the mixture, is preferred.

Various weight ratios of core material to wall material may be employed. The state of aggregation and nature of the core material and the diameter of the microcapsules may be a factor in this decision. In the preferred phase separation process, the ratio is in general from 1:1 to 30:1, preferably from 3:1 to 15:1. For a constant capsule diameter, the wall thickness is determined by the ratio of core material to wall material. The wall material may be crosslinked after carrying out the encapsulation. By this means, the degree of impermeability of the microcapsules, and the retarded vaporization of the active ingredient, can be controlled.

The aqueous dispersion of the capsules obtained from the microcapsule manufacturing process can be concentrated, for example by removing the excess water by distillation or centrifuging.

Where necessary, further additives may be incorporated into the microcapsule dispersion, e.g. thickeners, wetting agents and dispersants, binders, fillers or antifoam agents. For greater ease of storage it is possible to produce a dry microcapsule powder from the microcapsule dispersion. Various processes may be used for isolating the microcapsules from the dispersion and drying them, e.g. freeze-drying or drying on trays after isolating the microcapsules by sieving or centrifuging. A particularly suitable process is spray-drying. For this purpose, the capsule dispersion is sprayed in a spray-dryer, using a one-fluid or two-fluid nozzle or a whirler disc. If the drying gases are used at an input temperature of, for example, from 100° to 140° C. and an output temperature of, for example, from 50° to 70° C., a free-flowing dry powder is obtained. The individual capsules in the powder have the same diameters as in the dispersion. The size of the powder particles depends on the size of the spray droplets and the solids content of the dispersion. The powder is readily redispersible in water. Using this method, a dispersion of the microcapsules is reconstituted.

The Examples which follow illustrate the manufacture of the microcapsule dispersions and their advantageous application.

EXAMPLE 1

Using the preferred phase separation process, the wall materials and the microcapsule dispersion are essentially manufactured as described in German Laid- Open Application DOS No. 2,119,933 and German Published Application DAS No. 2,213,755.

71 parts by weight of tridemorph are dissolved in 6 parts by weight of isopropanol and 65 parts by weight of chloroform. This solution is thoroughly dispersed, at room temperature, in a solution of 50 parts by weight of a 10% strength aqueous polyvinylpyrrolidone solution (K value of the polyvinylpyrrolidone=90, measured on a 1% strength solution in water) and 200 parts by weight of water, the dispersing device used being an Ultra-Turrax from Jahnke and Kunkel. A solution of 60 parts by weight of a 40% strength wall material solution in chloroform/isopropanol, as described in Example 1 of German Laid-Open Application DOS No. 2,119,933, and 65 parts of chloroform is then added slowly at from 30° to 60° C., under constant thorough dispersion. The dispersion time is selected to give particles having a diameter of from 5 to 10 μm. The emulsion is diluted with 250 parts by weight of water in a distillation flask, whilst stirring, and the auxiliary solvents, i.e. the chloroform and isopropanol, are distilled off completely. The capsule wall is then hardened, in the course of 2 hours at 80° C., by adding 6 parts by weight of 40% strength formaldehyde solution.

A microcapsule dispersion which has a solids content of 18.5% by weight and a tridemorph content of 12.5% by weight is formed. The viscosity in a DIN cup (FB 4 mm), measured as the flow time, is 14.4 seconds. The microcapsules are spherical and have a mean diameter of from 6 to 10 μm. The cured wall material forms a capsule round the tridemorph.

The encapsulation is virtually complete; the proportion of free tridemorph outside the microcapsules is less then 0.03% by weight. The rate of vaporization of the active ingredient from the microcapsules is lower by a factor of 90 than that of the non-mixed, non-encapsulated active ingredient.

In order to ensure that the aqueous capsule dispersion is stable on storage, from 1 to 2% by weight of a 25% strength dispersion of a partially crosslinked copolymer containing carboxylic acid, as described in German Laid-Open Application DOS No. 2,217,690, can be added to the dispersion. The viscosity, measured with a Brookfield viscometer, spindle 4, at 100 rpm, is from 400 to 600 centipoise, whilst measured as the flow time from a DIN cup (FB 4 mm) it is from 40 to 50 sec.

To produce a dry powder, the aqueous micro-capsule dispersion is sprayed with air into a spray-dryer, using a two-fluid nozzle. Using a drying gas input temperature of 120° C., the amount of dispersion introduced into the spray-dryer is adjusted to give an output temperature of 60° C.

The dry powder thus obtained is readily redispersible.

The dry microcapsules have the same appearance as the capsules dispersed in water.

EXAMPLE 2

The procedure described in Example 1 is followed, but the tridemorph/isopropanol/chloroform solution to be encapsulated is added to the solution of wall material in chloroform. This tridemorph/wall material/chloroform/isopropanal solution is then dispersed in the aqueous polyvinylpyrrolidone solution, after which the encapsulation is completed, using the method already described, by removing the isopropanol and chloroform and then carrying out a treatment with formaldehyde. The microcapsules have a diameter of from 5 to 15 μm.

EXAMPLE 3

The procedure described in Example 1 is followed, but when distilling the isopropanol and chloroform, the material is not diluted with water in the distillation flask. Furthermore, the wall material used is a material prepared, as described in German Laid-Open Application DOS No. 2,119,933, by copolymerizing 20% by weight of propanediol monoacrylate acetylacetate, 50% by weight of methyl methacrylate and 30% by weight of acrylic acid. Under these conditions, the distillation of the auxiliary solvent takes place completely, without interfering with the microcapsules.

A microcapsule dispersion having a solids content of 34.8% by weight is obtained, while the proportion of free tridemorph outside the microcapsules is 0.015% by weight.

The microcapsule dispersion prepared as described in Examples 1 to 3 were tested for their biological activity, in comparison with non-encapsulated tridemorph.

EXAMPLE 4

Wheat mildew

Leaves of pot-grown wheat seedlings of the "Jubilar" variety are sprayed with aqueous microcapsule dispersions and after the spray coating has dried, the plants are dusted with oidiae (spores) of wheat mildew (*Erysiphe graminis* var. tritici). The test plants are then set up in a greenhouse at from 20° to 22° C. and from 75 to 80% relative atmospheric humidity. After 10 days, the degree of development of the mildew fungi, and the leaf damage, are determined. An aqueous tridemorph emulsion which contains 80% of active ingredient and 20% of emulsifier is used as the comparative agent.

| Microcapsule dispersion | Infection of the leaves after spraying with aqueous dispersions or emulsions; . . . % by weight of active ingredient in the spray liquor | | | | |
|---|---|---|---|---|---|
| | 0.1 | 0.05 | 0.025 | 0.012 | 0.006 |
| Example 1 | 0 | 1 | 2 | 3 | 3 |
| Example 3 | 0 | 0 | 1 | 1–2 | 3 |
| Non-encapsulated tridemorph (comparative agent) | 0(2D) | 1(1H) | 2 | 3–4 | 4 |
| Control (untreated) | 4 | | | | |

0 = no infection, graded up to 5 = total infection
0 = leaf damage: 2D = numerous leaf necroses; slight damage
1H = chlorosis; indication of damage.

EXAMPLE 5

Barley mildew

Using the procedure described in Example 4, barley plants of the "Asse" variety are treated, and dusted with oidiae (spores) of barley mildew (*Erysiphe graminis* var. hordei).

| Microcapsule dispersion | Infection of the leaves after spraying with aqueous dispersions or emulsions;. . .% by weight of active ingredient in the spray liquor | | | | |
|---|---|---|---|---|---|
| | 0.1 | 0.05 | 0.025 | 0.012 | 0.006 |
| Example 1 | 0 | 0 | 0 | 0 | 1 |
| Example 2 | 0 | 0 | 0 | 0 | 0 |
| Non-encapsulated tridemorph (comparative agent) | 0 (2-3AD) | 0 (1-2C) | 1 | 1 | 2 |

-continued

| Microcapsule dispersion | Infection of the leaves after spraying with aqueous dispersions or emulsions;. . .% by weight of active ingredient in the spray liquor 0.1 | 0.05 | 0.025 | 0.012 | 0.006 |
|---|---|---|---|---|---|
| Control | 4 | | | | |

0 = no infection, graded up to 5 = total infection
() = leaf damage: 2-3AD = numerous necroses; medium leaf damage
1-2C = some necroses; slight leaf damage.

It follows from the experimental results that the fungicides according to the invention show, compared to the non-encapsulated product, an improved fungicidal activity in some cases, together with improved tolerance.

EXAMPLE 6

To prepare very small microcapsules with a diameter of from 0.1 to 0.5 μm, 142 parts by weight of tridemorph are dissolved in 130 parts by weight of chloroform, using a method similar to that of Example 1. This solution is thoroughly dispersed, at room temperature, in a mixture of 66 parts by weight of "Texapon K 12" emulsifier from Dehydag, 400 parts by weight of water, 1.0 part by weight of tributylamine and 0.94 part by weight of p-toluene-sulfonic acid. A solution of 192 parts by weight of a 40% strength solution of wall material in chloroform/isopropanol, as described in Example 1 of German Laid-Open Application DOS No. 2,119,933, and 58 parts by weight of chloroform is then added slowly at 40° C., with constant thorough dispersing. After a dispersion time of one minute, the mean capsule diameter has assumed a value of from 0.1 to 0.5 μm.

The emulsion is diluted with 500 parts by weight of water and the chloroform and isopropanol are then distilled off completely.

The capsule wall is hardened by adding 8 parts by weight of 40% strength formaldehyde solution in the course of 2 hours at 80° C.

The microcapsule dispersion has a solids content of 16.5% by weight and a proportion of tridemorph of 12.5% by weight in the dispersion. The viscosity, measured by means of a Brookfield viscometer, spindle 1, at 100 revolutions per minute, is 16 mPas. It is possible to increase the viscosity, and spray-dry the material, as described in Example 1. Encapsulation is virtually complete; the proportion of tridemorph outside the microcapsules is less than 0.01% by weight.

The rate of vaporization of the active ingredient from the microcapsules is less by a factor of 165 than the rate of vaporization of the non-compounded, non-encapsulated active ingredient.

EXAMPLE 7

The encapsulation by the coacervation process was carried out using the process described in U.S. Pat. No. 2,800,457. 20 parts of pigskin gelatin are dissolved in 160 parts of water and 2.5 parts of carboxymethylcellulose are dissolved in 210 parts of water at 50° C., the solutions are mixed and the pH is brought to 6.0 by adding 10% strength sodium hydroxide solution. 67.5 parts of tridemorph are dispersed in the mixture of the two colloid solutions, using a Ultra-Turrax as the dispersing device, until the particle diameter has assumed a value of from 2 to 4 μm. The emulsion is diluted with 450 parts of water at 50° C., whilst stirring, and the pH is then lowered to 4.88 by adding 10% strength acetic acid. After the coacervated capsule has formed, 3.5 parts of 37% strength formaldehyde solution are added and the temperature of the dispersion is lowered to 5° C. to gel the wall material. For post-hardening, the pH is brought to 8.17 by adding 10% strength sodium hydroxide solution and the mixture is stirred for 12 hours at room temperature, i.e. 20° C.

With a tridemorph:wall material ratio of 75:25% by weight, the micro-capsule dispersion obtained has a solids content of 9.5% by weight and a viscosity of 11.3 seconds, measured as the flow time from a DIN cup (FB 4).

The dispersion can be concentrated to a solids content of from about 20 to 50% by weight, by centrifuging. To prepare a dry powder, either the initial dispersion or the concentrated dispersion can be spray-dried as described in Example 1.

EXAMPLE 8

Microencapsulation on the interfacial polycondensation principle is carried out essentially by the process described in U.S. Pat. No. 3,429,827.

A solution of 25 parts of terephthalic acid dichloride in 44 parts of di-n-butyl phthalate and 44 parts of tridemorph is emulsified in an aqueous solution of 4 parts of polyvinyl alcohol and 0.1 part of sodium pyrophosphate, using an Ultra-Turrax as the dispersing device. Immediately thereafter, an aqueous solution of 8 parts of ethylenediamine, 0.5 part of 1,6-hexamethylenediamine, 10.3 parts of diethylenetriamine, 10 parts of sodium hydroxide solution and 75 parts of water is added, with continuous emulsifying. The mixture is then stirred for 12 hours in a flask, using a low-speed stirrer.

A microcapsule dispersion with particle diameters of from 3 to 6 μm is obtained. The solids content is about 30% by weight. The viscosity is 12.75 seconds, measured as the flow time from a DIN cup (FB 4).

We claim:

1. A fungicide containing N-tridecyl-2,6-dimethylmorpholine as the active ingredient, comprising microcapsules which contain the active ingredient and a phthalate plasticizer having a boiling point between about 100° C. and about 250° C. in their core whilst their walls consist of a crosslinked or a formaldehyde hardened or cured non-crosslinked synthetic or natural polymer or a mixture of such polymers, said walls being sufficiently impermeable to retard the vaporization of the active ingredient.

2. A fungicide as claimed in claim 1 wherein said phthalate plasticizer is present in a proportion of from 0% to 50% by weight, based on the weight of said mixture.

3. A fungicide as claimed in claim 2 wherein the weight ratio of said mixture of N-tridecyl-2,6-dimethylmorpholine and phthalate plasticizer to said wall material is from 3:1 to 15:1.

4. A fungicide as claimed in claim 1 in the form of an aqueous microcapsule dispersion.

5. A fungicide as claimed in claim 1 in the form of a dry microcapsule powder.

* * * * *